US006752018B2

(12) United States Patent
Goldmeer et al.

(10) Patent No.: US 6,752,018 B2
(45) Date of Patent: Jun. 22, 2004

(54) METHOD AND APPARATUS FOR CHARACTERIZING AN ACOUSTIC IMPEDANCE

(75) Inventors: Jeffrey Scott Goldmeer, Colonie, NY (US); Simon Ralph Sanderson, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 32 days.

(21) Appl. No.: 10/159,267

(22) Filed: Jun. 3, 2002

(65) Prior Publication Data

US 2003/0221488 A1 Dec. 4, 2003

(51) Int. Cl.[7] ............................................... G01N 29/16
(52) U.S. Cl. .......................................... 73/589; 73/645
(58) Field of Search ........................ 73/589, 660, 602, 73/645

(56) References Cited

U.S. PATENT DOCUMENTS

| | | | | |
|---|---|---|---|---|
| 4,732,039 A | * | 3/1988 | Syed ............................ | 73/589 |
| 6,119,521 A | * | 9/2000 | Shivashankara et al. ....... | 73/589 |
| 6,134,968 A | * | 10/2000 | Kunze et al. .................. | 73/589 |

OTHER PUBLICATIONS

David F. Ross, et al. "Measurement of the Acoustic Internal Source Impedance of an Internal Combustion Engine", J. Acoust. Soc. Am 74 (1), Jul. 1983, pp. 18–27.

"Standard Test Method for Impedance and Absorption of Acoustical Materials Using a Tube, Two Microphones and a Digital Frequency Analysis System", American Society for Testing and Materials (ASTM) Standard, Designation: E 1050–98, pp. 951–961.

Jy Chung, et al., "Transfer Function Method for Measuring In–Duct Acoustic Properties. I. Theory", J. Acoust. Soc. Am. 68(3), Sep. 1980, pp. 907–913.

Jy Chung, et al., "Transfer Function Method of Measuring In–Duct Acoustic Properties. II. Experiment", J. Acoust. Soc. Am. 68(3), Sep. 1980, pp. 914–921.

* cited by examiner

*Primary Examiner*—Hezron Williams
*Assistant Examiner*—Nashmiya Fayyaz
(74) *Attorney, Agent, or Firm*—Patrick K. Patnode; Christian G. Cabou

(57) ABSTRACT

In one embodiment of the present invention, an apparatus for characterizing an acoustic impedance of an engineering component acoustically coupled to an acoustic waveguide includes: a pressure measurement apparatus adapted to be moved and to be disposed to measure pressure signals, the pressure signals being measured at respective ones of a plurality of predetermined locations along the acoustic waveguide; an exciter adapted to excite the acoustic waveguide with an excitation signal; a data collection module adapted to incorporate the pressure signals from the pressure measurement apparatus into a pressure signal set; a transform module adapted to transform the pressure signal set to a frequency domain set; a wave shape identifier adapted to identify a plurality of wave shape parameters from the frequency domain set; and a statistical computer adapted to compute from the frequency domain set a statistical measure for the wave shape parameters, the statistical measure being selected from the group consisting of residual variance, correlation coefficient, F-statistic, p-statistic, and confidence interval.

48 Claims, 2 Drawing Sheets

METHOD AND APPARATUS FOR CHARACTERIZING AN ACOUSTIC IMPEDANCE

BACKGROUND

The present invention relates generally to the field of characterizing an acoustic impedance and, more specifically, to the use of multiple pressure measurements using the same pressure transducer at different locations along a one dimensional acoustic waveguide terminated in the acoustic impedance to be characterized.

In a wide variety of applications, it is advantageous to characterize an acoustic impedance of a component of an engineering system, typically with a view toward modifying the component, or other interacting components, to eliminate an undesirable acoustic behavior. For example, anytime a flame is caused to burn in a confined space, a possibility exists that heat release dynamics of the flame will interact with an acoustic impedance of the confined space to produce a phenomenon known as combustion instability.

Combustion instability manifests itself as a sustained, self-excited pressure oscillation often of sufficient amplitude to be damaging to structural elements within the confined space. A gas turbine engine provides a typical example of an engineering system prone to damage by combustion instability. Knowledge of the acoustic impedance of a gas turbine engine combustor provides a designer an opportunity to reduce the likelihood of combustion instability by altering, for example, the combustor geometry. Whereas this disclosure emphasizes embodiments of the present invention applicable to a gas turbine engine, it will be obvious to one of ordinary skill in the art that the present invention is equally applicable to a wide variety of other engineering systems where acoustic impedance characterization is important.

Conventional techniques for characterizing an acoustic impedance of an engineering component involve: mounting the engineering component at one end of a one-dimensional acoustic waveguide; coupling a plurality of pressure transducers to the waveguide at various fixed locations along the waveguide; acoustically exciting the waveguide; collecting pressure measurement data; and reducing the pressure measurement data to produce an acoustic impedance estimate. However, such conventional techniques suffer a number of shortcomings.

First, any coupling apparatus interposed between a pressure transducer and the waveguide has a parasitic coupling impedance that affects the accuracy of the ultimate acoustic impedance estimate. For example, when characterizing an operating gas turbine engine combustor, it is often desirable to couple the pressure transducers to the waveguide through coupling tubes long enough to remove the pressure transducers to a safe ambient temperature. The parasitic coupling impedances of the coupling tubes then provide a significant source of error. In some cases, it may be possible to perform additional experiments to characterize these parasitic coupling impedances and reduce the error, but such additional experiments represent an additional cost of the technique. An opportunity exists, therefore, to improve accuracy and reduce cost by finding an acoustic impedance characterization method that is insensitive to parasitic coupling impedances without performing additional experiments.

Second, many conventional approaches to impedance estimation assume no knowledge of the mathematical relationships among the multiple pressure measurements acquired. Such approaches are essentially non-parametric approaches and are prone to yielding poorer results than parametric approaches utilizing a priori information about wave propagation in the acoustic waveguide. An opportunity exists, therefore, to further improve accuracy by finding an acoustic characterization method that exploits a priori knowledge of the wave shapes of the acoustic waveguide.

Third, the acoustic impedance estimate produced by conventional data reduction techniques is typically a "point estimate," i.e., a single instance of an acoustic impedance measurement without regard to the statistical nature of the measurement process. When using such conventional data reduction techniques to compare acoustic impedances of two presumably different designs, a designer has no way of gauging whether any perceived variation is due to a true difference in the designs or due to inherent variability in the measurement process. An opportunity exists, therefore, to provide a more useful acoustic impedance estimate by providing additional estimates of the statistical reliability of the acoustic impedance estimate.

SUMMARY

The opportunities described above are addressed, in one embodiment of the present invention, by an apparatus for characterizing an acoustic impedance of an engineering component acoustically coupled to an acoustic waveguide, the apparatus comprising: a pressure measurement apparatus adapted to be moved and to be disposed to measure pressure signals, the pressure signals being measured at respective ones of a plurality of predetermined locations along the acoustic waveguide; an exciter adapted to excite the acoustic waveguide with an excitation signal; a data collection module adapted to incorporate the pressure signals from the pressure measurement apparatus into a pressure signal set; a transform module adapted to transform the pressure signal set to a frequency domain set; a wave shape identifier adapted to identify a plurality of wave shape parameters from the frequency domain set; and a statistical computer adapted to compute from the frequency domain set a statistical measure for the wave shape parameters, the statistical measure being selected from the group consisting of residual variance, correlation coefficient, F-statistic, p-statistic, and confidence interval.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
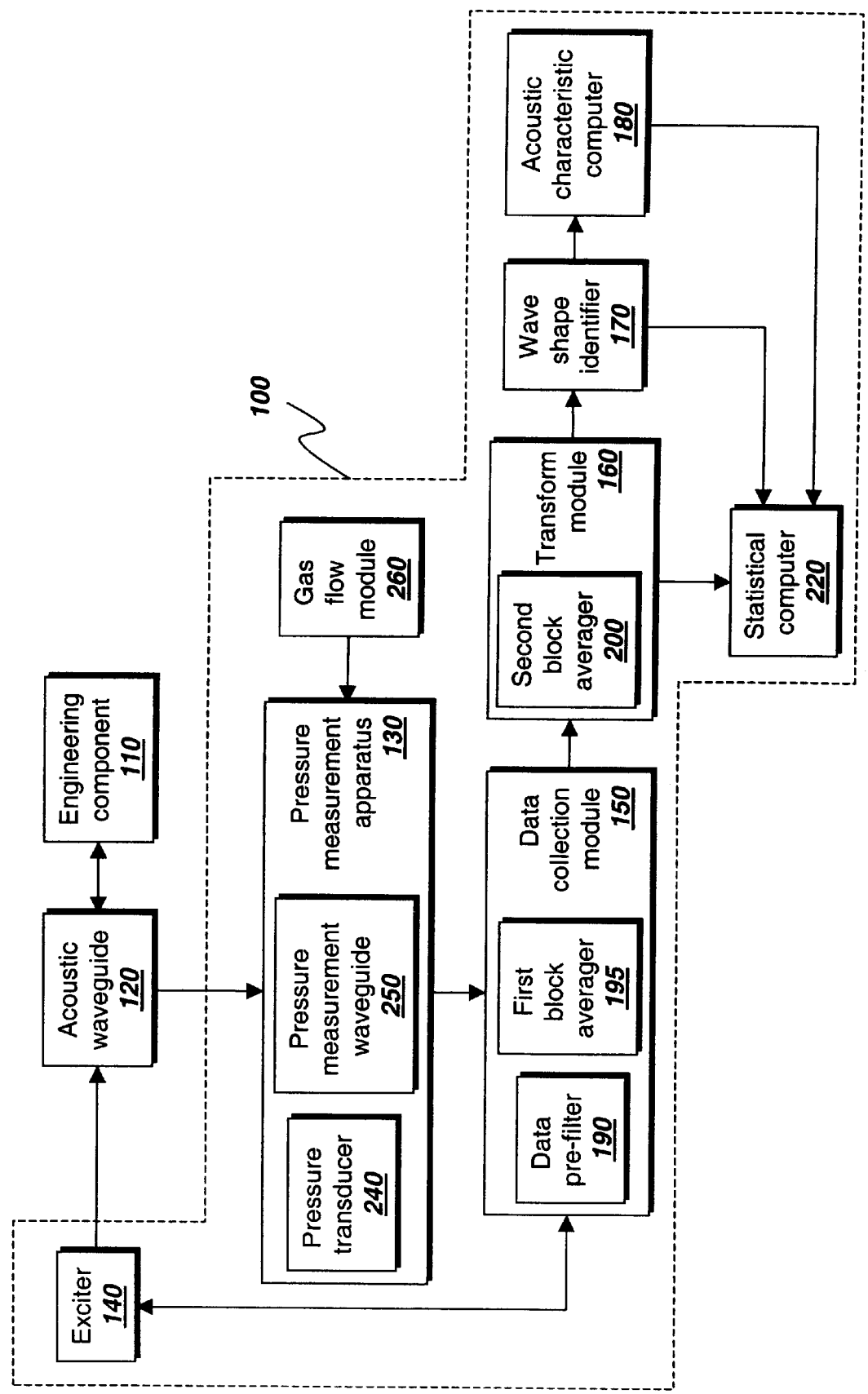
FIG. 1 illustrates a block diagram of an apparatus for characterizing an acoustic impedance of an engineering component in accordance with one embodiment of the present invention.

In accordance with one embodiment of the present invention, FIG. 1 illustrates a block diagram of an apparatus 100 for characterizing an acoustic impedance of an engineering component 110. Apparatus 100 comprises an acoustic waveguide 120, a pressure measurement apparatus 130, an exciter 140, a data collection module 150, a transform module 160, a wave shape identifier 170, and an acoustic characteristic computer 180.

In response to an excitation command generated by data collection module 150, exciter 140 excites acoustic waveguide 120 with an excitation signal giving rise to pressure fluctuations acoustically coupled through acoustic waveguide 120 to engineering component 110. Pressure measurement apparatus 130 is disposed to measure a pressure signal at one of a plurality of predetermined locations along acoustic waveguide 120. The pressure signal is then incorporated, coherently with the excitation signal, into a pressure signal set by data collection module 150. The steps of exciting acoustic waveguide 120, disposing pressure measurement apparatus 130, and incorporating the measured pressure signal are repeated at each other one of the predetermined locations to complete the pressure signal set, $p(x_j,t)$, $j=1 \ldots N$, where $x_j$, t are real numbers corresponding to the predetermined locations along acoustic waveguide 120 and time, respectively, and N is the number of predetermined locations. Transform module 160 then transforms the pressure signal set to a frequency domain set, $\tilde{P}(x_j,\omega)$, $j=1 \ldots N$ where $\tilde{P}(x_j,\omega)$ is a complex number corresponding to the Fourier transform of $p(x_j,t)$, and $\omega$ is a real number corresponding to frequency.

From the frequency domain set, wave shape identifier 170 identifies a plurality of wave shape parameters corresponding to wave propagation modes of acoustic waveguide 120. By way of example, but not limitation, acoustic waveguide 120 may comprise a one-dimensional waveguide for which the frequency domain set satisfies;

$$i\,\tilde{P}(x_j,\omega) = \tilde{A}(\omega)e^{-ik_i x_j} + \tilde{B}(\omega)e^{ik_r x_j},\ j=1 \ldots N,$$

where $i=\sqrt{-1}$; $\tilde{A}(\omega)$, $\tilde{B}(\omega)$ are complex numbers corresponding to the wave shape parameters; and $k_i=k/(1+M)$, $k_r=k/(1-M)$, $k=\omega/c$, M, c are real numbers corresponding to incident wave number, reflected wave number, wave number without flow, mean flow Mach number and, sound speed, respectively. The wave shape parameters may be identified by finding a least squares solution to the matrix equation $\underline{P}(\omega)=\underline{\underline{X}}(\omega)\,\underline{\beta}(\omega)$, where:

$$\underline{P} = \begin{bmatrix} P_{1,Re}(\omega) \\ P_{1,Im}(\omega) \\ P_{2,Re}(\omega) \\ P_{2,Im}(\omega) \\ \vdots \\ P_{N,Re}(\omega) \\ P_{N,Im}(\omega) \end{bmatrix},$$

$$\underline{\underline{X}} = \begin{bmatrix} \cos k_i x_1 & \sin k_i x_1 & \cos k_r x_1 & -\sin k_r x_1 \\ -\sin k_i x_1 & \cos k_i x_1 & \sin k_r x_1 & \cos k_r x_1 \\ \cos k_i x_2 & \sin k_i x_2 & \cos k_r x_2 & -\sin k_r x_2 \\ -\sin k_i x_2 & \cos k_i x_2 & \sin k_r x_2 & \cos k_r x_2 \\ \vdots & \vdots & \vdots & \vdots \\ \cos k_i x_N & \sin k_i x_N & \cos k_r x_N & -\sin k_r x_N \\ -\sin k_i x_N & \cos k_i x_N & \sin k_r x_N & \cos k_r x_N \end{bmatrix},$$

$$\underline{\beta} = \begin{bmatrix} A_{Re}(\omega) \\ A_{Im}(\omega) \\ B_{Re}(\omega) \\ B_{Im}(\omega) \end{bmatrix},$$

$P_{j,Re}(\omega)=Re[\tilde{P}(x_j,\omega)]$, $P_{j,Im}(\omega)=Im[\tilde{P}(x_j,\omega)]$, $A_{Re}(\omega)=Re[\tilde{A}(\omega)]$, $A_{Im}(\omega)=Im[\tilde{A}(\omega)]$, $B_{Re}(\omega)=Re[\tilde{B}(\omega)]$, $B_{Im}(\omega)=Im[\tilde{B}(\omega)]$.

The least squares solution is given by $\underline{\beta}=\underline{\underline{C}}\underline{\underline{X}}^T\underline{P}$, where $\underline{\underline{C}}=[\underline{\underline{X}}^T\underline{\underline{X}}]^{-1}$ and the superscript "T" denotes the transpose of a matrix or vector.

From the wave shape parameters, acoustic characteristic computer 180 then completes the characterization by computing acoustic characteristics such as: acoustic impedance:

$$\tilde{Z}(\omega) = \rho c \left[ \frac{\tilde{A}(\omega) + \tilde{B}(\omega)}{\tilde{A}(\omega) - \tilde{B}(\omega)} \right],$$

where $\rho$ is a real number corresponding to fluid density; reflection coefficient:

$$R = \frac{|\tilde{B}(\omega)|}{|\tilde{A}(\omega)|};$$

transmission coefficient $T=1-R$; and impulse response which is the inverse Fourier transform of $\tilde{Z}(\omega)$.

All of the pressure signal measurements are performed using the same pressure measurement apparatus 130, moved serially to each of the predetermined locations, and the same excitation signal, and are incorporated coherently with the excitation signal. (As used herein, "incorporating coherently with the excitation signal" refers to recording the pressure signals such that all pressure signals start at the same time relative to the start of the excitation signal. Coherent incorporation requires communication between exciter 140 and data collection module 150 so that one may trigger operation of the other.) When transformed to the frequency domain, all frequency domain signals are therefore multiplied by a common factor comprising a product of the excitation signal spectrum and the pressure measurement apparatus frequency response. In the subsequent calculation of the acoustic characteristics, however, the common factor divides out, obviating the need either to measure the excitation signal or to calibrate pressure measurement apparatus 130.

Acoustic waveguide 120 comprises any device or structure filled with a fluid, typically air, capable of transmitting pressure waves (acoustic waves) through the fluid and whose acoustic wave shapes are known. Examples of acoustic waveguide 120 include, without limitation, pipes and tubing. Exemplary embodiments of pressure measurement apparatus 130 typically comprise a means of acoustically coupling to acoustic waveguide 120 and a means of generating a pressure signal as a function of a pressure within acoustic waveguide 120. Exemplary means of acoustically coupling to acoustic waveguide 120 include, without limitation, pipes and tubing. Exemplary means of generating a pressure signal include, without limitation, pressure sensors, pressure transducers and microphones including, without limitation, those based on piezoresistive and piezoelectric materials and those utilizing pistons, mechanical deflection, strain gauges, micro-electro-mechanical systems (MEMS), variable capacitance, and vibrating elements.

Exciter 140 comprises any device or combination of devices capable of repeatably inducing pressure fluctuations in acoustic waveguide 120. Examples of exciter 140 include, without limitation, loudspeakers, spark plugs and valves including, without limitation, proportional valves, servovalves, and solenoid valves. In a reacting system, such as an operating gas turbine combustor, exciter 140 may control a fuel flow or ignition thereof.

Data collection module 150, transform module 160, wave shape identifier 170, and acoustic characteristic computer 180 comprise any electronic device or combination of devices capable of performing the required computations. Examples of data collection module 150, transform module 160, wave shape identifier 170, and acoustic characteristic computer 180 include, without limitation, analog electronic computation modules and digital electronic computation modules (digital computers) including, without limitation, array processors, microcomputers, microprocessors, microcontrollers, and single-chip digital signal processors (DSPs). In typical embodiments, data collection module 150, transform module 160, wave shape identifier 170, and acoustic characteristic computer 180 are implemented in software in a single digital computer.

In accordance with a more detailed embodiment of the present invention, the excitation signal is periodic, data collection module 150 comprises a data pre-filter 190 and a first block averager 195, and wave shape identifier 170 comprises a second block averager 200. Because the excitation signal is periodic, the measured pressure signals are also periodic with the same period. Data pre-filter 190 discards a portion of the pressure signal, typically the beginning portion corresponding to any transient pressure response and typically comprising an integral number of cycles (periods). First block averager 195 block averages the pressure signal, and second block averager 200 block averages the frequency domain set. As used herein, "block averaging" refers to a process comprising: identifying a plurality of data blocks, each of the data blocks comprising the same integral number of cycles; adding corresponding data points from each of the data blocks to form a summed data block; and dividing each element of the summed data block by the number of data blocks to form an averaged data block. Because the pressure signals are incorporated coherently with the excitation signal, any difference in value between corresponding points in different blocks is due to measurement noise assumed to be uncorrelated among the data blocks so that the noise variance is reduced by averaging.

In another more detailed embodiment in accordance with the embodiment of FIG. 1, apparatus 100 further comprises a statistical computer 220. Statistical computer 220 computes from the frequency domain set a statistical measure for the wave shape parameters, the statistical measure being selected from the group consisting of residual variance, correlation coefficient, F-statistic, p-statistic, confidence interval, and combinations thereof. Continuing the example above wherein acoustic waveguide 120 is one-dimensional, the residual variance $$\sigma^2_{resid}$$

is given by:

$$\sigma^2_{resid} = \frac{P^T P - \beta^T X^T P}{2N - K - 1},$$

where K=4 is the number of regressed coefficients; the correlation coefficient $R^2$ is given by:

$$R^2 = \frac{\beta^T X^T P}{P^T P};$$

the F-statistic F is given by:

$$F = \frac{\beta^T X^T P}{P^T P - \beta^T X^T P} \cdot \frac{2N - K - 1}{K};$$

the p-statistic p is given by:

$$p = 1/F;$$

and the confidence interval is given by:

$$\beta_i(\omega) \pm t \cdot C_{ii} \sigma^2_{resid}, \; i = 1 \ldots 4$$

where t is computed from Student's t-distribution as a function of a desired confidence level and the number of degrees of freedom 2N−K−1.

In another embodiment in accordance with the embodiment of FIG. 1, statistical computer 220 also computes a statistical measure for the acoustic characteristics, the statistical measure being selected from the group consisting of residual variance, correlation coefficient, F-statistic, p-statistic, confidence interval, and combinations thereof.

Figure 2:
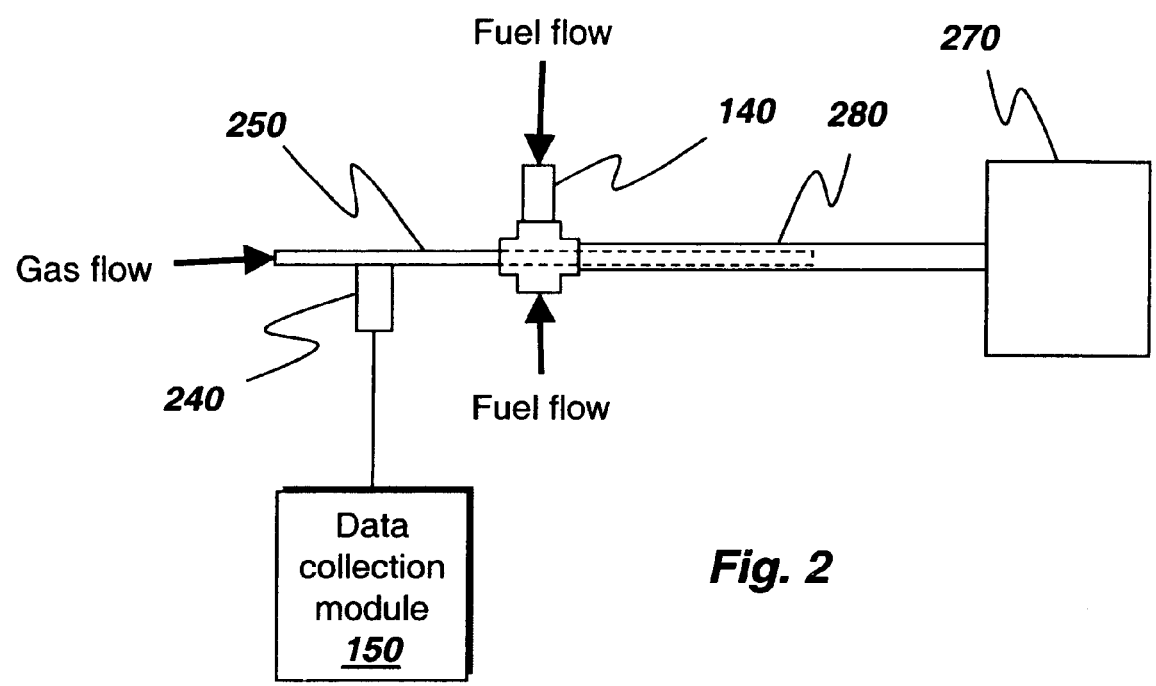
FIG. 2 illustrates a schematic drawing of an apparatus for characterizing an acoustic impedance of a gas turbine combustor in accordance with another embodiment of the present invention.

In accordance with a more detailed embodiment of the embodiment of FIG. 1, FIG. 2 illustrates a schematic drawing of an apparatus for characterizing an acoustic impedance of a gas turbine combustor wherein engineering component 110 comprises a gas turbine combustor 270, acoustic waveguide 120 comprises a combustor inlet 280, pressure measurement apparatus 130 comprises a pressure transducer 240 and a pressure measurement waveguide 250, and a gas flows through pressure measurement waveguide 250. Pressure measurement waveguide 250 acoustically couples to pressure transducer 240 and couples pressure at the predetermined locations along combustor inlet 280. Examples of pressure transducer 240 and pressure measurement waveguide 250 are described above. Pressure measurement waveguide 250 is substantially concentric with combustor inlet 280. As used herein, "substantially concentric" refers to the property that a longitudinal axis of pressure measurement waveguide 250 is substantially parallel to a longitudinal axis of combustor inlet 280 and that a portion of pressure measurement waveguide 250 is disposed inside combustor inlet 280. The gas flow serves to cool pressure measurement waveguide 250, thereby protecting pressure transducer 240 from excessive temperature, and to maintain a uniform temperature and a uniform composition therein, thereby improving pressure signal measurement accuracy.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for characterizing an acoustic impedance of an engineering component acoustically coupled to an acoustic waveguide, said method comprising:

disposing a pressure measurement apparatus to measure pressure at one of a plurality of predetermined locations along said acoustic waveguide;

exciting said acoustic waveguide with an excitation signal;

incorporating a pressure signal from said pressure measurement apparatus into a pressure signal set;

performing said steps of disposing, exciting, and incorporating using said pressure measurement apparatus and said excitation signal at each other one of said plurality of predetermined locations;

transforming said pressure signal set to a frequency domain set;

identifying a plurality of wave shape parameters from said frequency domain set; and computing from said frequency domain set a statistical measure for said wave shape parameters, said statistical measure being selected from the group consisting of residual variance, correlation coefficient, F-statistic, p-statistic, and confidence interval and wherein an acoustic impedance is computed.

2. The method of claim 1 wherein said step of incorporating said pressure signal comprises incorporating said pressure signal coherently with said excitation signal.

3. An apparatus for characterizing an acoustic impedance of a gas turbine combustor acoustically coupled to a combustor inlet, said apparatus comprising:

a pressure measurement apparatus adapted to be moved and to be disposed to measure pressure signals, said pressure signals being measured at respective ones of a plurality of predetermined locations along said combustor inlet, said pressure measurement apparatus comprising a pressure transducer and a pressure measurement waveguide acoustically coupled to said pressure transducer and adapted to couple pressure at said predetermined locations along said combustor inlet;

a gas flow module adapted to flow a gas through said pressure measurement waveguide;

an exciter adapted to excite said combustor inlet with an excitation signal;

a data collection module adapted to incorporate, coherently with said excitation signal, said pressure signals from said pressure measurement apparatus into a pressure signal set;

a transform module adapted to transform said pressure signal set to a frequency domain set;

a wave shape identifier adapted to identify a plurality of wave shape parameters from said frequency domain set;

an acoustic impedance to computer adapted to compute an acoustic impedance from said wave shape parameters; and a statistical computer adapted to compute from said frequency domain set a statistical measure for said acoustic impedance, said statistical measure being selected from the group consisting of residual variance, correlation coefficient, F-statistic, p-statistic, and confidence interval.

4. The apparatus of claim 3 wherein said excitation signal is periodic.

5. The method of claim 1 wherein said excitation signal is periodic.

6. The method of claim 5 wherein said step of incorporating comprises discarding a portion of said pressure signal.

7. The method of claim 5 wherein said step of incorporating comprises block averaging said pressure signal.

8. The method of claim 5 wherein said step of identifying comprises block averaging said frequency domain set.

9. The method of claim 1 wherein said pressure measurement apparatus comprises:

a pressure transducer; and a pressure measurement waveguide acoustically coupled to said pressure transducer and adapted to couple pressure at said predetermined locations along said acoustic waveguide.

10. The method of claim 9 further comprising flowing a gas through said pressure measurement waveguide.

11. The method of claim 9 wherein said pressure measurement waveguide is substantially concentric with said acoustic waveguide.

12. A method for characterizing an acoustic impedance of a gas turbine combustor acoustically coupled to a combustor inlet, said method comprising:

disposing a pressure measurement apparatus to measure pressure at one of a plurality of predetermined locations along said combustor inlet;

exciting said combustor inlet with an excitation signal;

incorporating, coherently with said excitation signal, a pressure signal from said pressure measurement apparatus into a pressure signal set;

performing said steps of disposing, exciting, and incorporating using said pressure measurement apparatus and said excitation signal at each other one of said plurality of predetermined locations;

transforming said pressure signal set to a frequency domain set;

identifying a plurality of wave shape parameters from said frequency domain set;

computing from said frequency domain set a statistical measure for said wave shape parameters, said statistical measure being selected from the group consisting of residual variance, correlation coefficient, F-statistic, p-statistic, and confidence interval;

computing an acoustic impedance from said wave shape parameters;

computing from said frequency domain set a statistical measure for said acoustic impedance said statistical measure being selected from the group consisting of residual variance, correlation coefficient, F-statistic, p-statistic, and confidence interval.

13. The method of claim 12 wherein said excitation signal is periodic.

14. The method of claim 13 wherein said step of incorporating comprises discarding a portion of said pressure signal.

15. The method of claim 13 wherein said step of incorporating comprises block averaging said pressure signal.

16. The method of claim 13 wherein said step of identifying comprises block averaging said frequency domain set.

17. The method of claim 12 wherein said pressure measurement apparatus comprises:

a pressure transducer; and a pressure measurement waveguide acoustically coupled to said pressure transducer and adapted to couple pressure at said predetermined locations along said combustor inlet.

18. The method of claim 17 further comprising flowing a gas through said pressure measurement waveguide.

19. The method of claim 17 wherein said pressure measurement waveguide is substantially concentric with said combustor inlet.

20. The apparatus of claim 4 wherein said data collection module comprises a data pre-filter adapted to discard a portion of said pressure signals.

21. The apparatus of claim 4 wherein said data collection module comprises a first block averager adapted to block average said pressure signals.

22. The apparatus of claim 4 wherein said wave shape identifier comprises a second block averager adapted to block average said frequency domain set.

23. The apparatus of claim 3 wherein said pressure measurement waveguide is substantially concentric with said combustor inlet.

24. An apparatus for characterizing an acoustisc impedance of a gas turbine combustor acoustically coupled to a combustor inlet, said apparatus comprising:

a pressure measurement apparatus adapted to be moved and to be disposed to measure pressure signals, said pressure signals being measured at respective ones of a plurality of predetermined locations along said combustor inlet;

an exciter adapted to excite said combustor inlet with an excitation signal;

a data collection module adapted to incorporate, coherently with said excitation signal, said pressure signals from said pressure measurement apparatus into a pressure signal set;

a transform module adapted to transform said pressure signal set to a frequency domain set;

a wave shape identifier adapted to identify a plurality of wave shape parameters from said frequency domain set;

an acoustic impedance computer adapted to compute an acoustic impedance from said wave shape parameters; and a statistical computer adapted to compute from said frequency domain set a statistical measure for said wave shape parameters, said statistical measure being selected from the group consisting of residual variance, correlation coefficient, F-statistic, p-statistic, and confidence interval, and a statistical measure for said acoustic impedance, said statistical measure being selected from the group consisting of residual variance, correlation coefficient, F-statistic, p-statistic, and confidence interval.

25. The apparatus of claim 24 wherein said excitation signal is periodic.

26. The apparatus of claim 25 wherein said data collection module comprises a data pre-filter adapted to discard a portion of said pressure signals.

27. The apparatus of claim 25 wherein said data collection module comprises a first block averager adapted to block average said pressure signals.

28. The apparatus of claim 25 wherein said wave shape identifier comprises a second block averager adapted to block average said frequency domain set.

29. A method for characterizing an acoustic impedance of a gas turbine combustor acoustically coupled to a combustor inlet, said method comprising:

disposing a pressure measurement apparatus to measure pressure at one of a plurality of predetermined locations along said combustor inlet, said pressure measurement apparatus comprising a pressure transducer and a pressure measurement waveguide acoustically coupled to aid pressure transducer and adapted to couple pressure at said predetermined locations along said combustor inlet;

flowing a gas through said pressure measurement waveguide;

exciting said combustor inlet with an excitation signal;

incorporating, coherently with said excitation signal, a pressure signal from said pressure measurement apparatus into a pressure signal set;

performing said steps of disposing, exciting, and incorporating using said pressure measurement apparatus and said excitation signal at each other one of said plurality of predetermined locations;

transforming said pressure signal set to a frequency domain set;

identifying a plurality of wave shape parameters from said frequency domain set;

computing an acoustic impedance from said wave shape parameters;

computing from said frequency domain set a statistical measure for said acoustic impedance, said statistical measure being selected from the group consisting of residual variance, correlation coefficient, F-statistic, p-statistic, and confidence interval.

30. The method of claim 29 wherein said excitation signal is periodic.

31. The method of claim 30 wherein said step of incorporating comprises discarding a portion of said pressure signal.

32. The method of claim 30 wherein said step of incorporating comprises block averaging said pressure signal.

33. The method of claim 30 wherein said step of identifying comprises block averaging said frequency domain set.

34. The method of claim 29 wherein said pressure measurement waveguide is substantially concentric with said combustor inlet.

35. An apparatus for characterizing an acoustic impedance of engineering component acoustically coupled to an acoustic waveguide, said apparatus comprising:

a pressure measurement apparatus adapted to be moved and to be disposed to measure pressure signals, said pressure signals being measured at respective ones of a plurality of predetermined locations along said acoustic waveguide;

an exciter adapted to excite said acoustic waveguide with an excitation signal;

a data collection module adapted to incorporate said pressure signals from said pressure measurement apparatus into a pressure signal set;

a transform module adapted to transform said pressure signal set to a frequency domain set;

a wave shape identifier adapted to identify a plurality of wave shape parameters from said frequency domain set; and a statistical computer adapted to compute from said frequency domain set a statistical measure for said wave shape parameters, said statistical measure being selected from the group consisting of residual variance, correlation coefficient, F-statistic, p-statistic, and confidence interval and wherein an acoustic impedance is computed.

36. The apparatus of claim 35 wherein said data collection module is further adapted to incorporate said pressure signals coherently with said excitation signal.

37. The apparatus of claim 35 further comprising an acoustic impedance computer adapted to compute an acoustic impedance from said waver parameters.

38. The apparatus of claim 37 wherein said statistical computer is further adapted to compute from said frequency domain set a statistical measure for said acoustic impedance, said statistical measure being selected from the group consisting of residual variance, correlation coefficient, F-statistic, p-statistic, and confidence interval.

39. The apparatus of claim 35 wherein said excitation signal is periodic.

40. The apparatus of claim 39 wherein said data collection module comprises a data pre-filter adapted to discard a portion of said pressure signals.

41. The apparatus of claim 39 wherein said data collection module comprises a first block averager adapted to block average said pressure signals.

42. The apparatus of claim 39 wherein said wave shape identifier comprises a second block averager adapted to block average said frequency domain set.

43. The apparatus of claim 35 wherein said pressure measurement apparatus comprises:
   a pressure transducer; and
   a pressure measurement waveguide acoustically coupled to said pressure transducer and adapted to couple pressure at said predetermined locations along said acoustic waveguide.

44. The apparatus of claim 43 further comprising a gas flow module adapted to flow a gas through said pressure measurement waveguide.

45. The apparatus of claim 43 wherein said pressure measurement waveguide is substantially concentric with said acoustic waveguide.

46. The apparatus of claim 24 wherein said pressure measurement apparatus comprises:
   a pressure transducer; and
   a pressure measurement waveguide acoustically coupled to said pressure transducer and adapted to couple pressure at said predetermined locations along said combustor inlet.

47. The apparatus of claim 46 further comprising a gas flow module adapted to flow a gas through said pressure measurement waveguide.

48. The apparatus of claim 46 wherein said pressure measurement waveguide is substantially concentric with said combustor inlet.

* * * * *